(12) United States Patent
Wang et al.

(10) Patent No.: US 8,445,279 B2
(45) Date of Patent: May 21, 2013

(54) CULTURED CELL CONSTRUCTION CONTAINING SPHEROIDS OF MESENCHYMAL STEM CELLS AND UTILIZATION THEREOF

(75) Inventors: Wenjie Wang, Tokyo (JP); Keiji Itaka, Toshima-ku (JP); Shinsuke Ohba, Cambridge, MA (US); Nobuhiro Nishiyama, Kita-ku (JP); Ung-il Chung, Arakawa-ku (JP); Yuichi Yamasaki, Bunkyo-ku (JP); Kazunori Kataoka, Nakano-ku (JP)

(73) Assignee: Transparent Inc., Chiba (JP)

( * ) Notice: Subject to any disclaimer, the term of this patent is extended or adjusted under 35 U.S.C. 154(b) by 1079 days.

(21) Appl. No.: 12/255,342

(22) Filed: Oct. 21, 2008

(65) Prior Publication Data

US 2010/0099190 A1 Apr. 22, 2010

(51) Int. Cl.
 *C12N 5/00* (2006.01)
 *C12N 5/02* (2006.01)
 *C12N 5/071* (2010.01)

(52) U.S. Cl.
 USPC ........... 435/395; 435/325; 435/366; 435/372; 435/402

(58) Field of Classification Search
 None
 See application file for complete search history.

(56) References Cited

U.S. PATENT DOCUMENTS 5,976,826 A * 11/1999 Singhvi et al. ................. 435/29

OTHER PUBLICATIONS

Takezawa et al. (1992) Morphological and immuno-cytochemical characterization of a hetero-spheroid composed of fibroblasts and hepatocytes. Journal of Cell Science 101: 495-501.*
Rossi et al. (2005) Multicellular spheroids of bone marrow stromal cells: a three-dimensional in vitro culture system for the study of hematopoietic cell migration. Brazilian Journal of Medical and Biological Research 38: 1455-1462.*
van Kooten et al. (1992) Influence of substratum wettability on the strength of adhesion of human fibroblasts. Biomaterials 13(13): 897-904.*
Wenjie Wang et al., "Improving mulitpotent differentiation efficiency of Mesenchymal Stem Cells using 3D spheroids method on microarray substrates", The 3rd SNU-UT-TU Student Workshop, Oct. 25, 2007, pp. 66-69.

* cited by examiner

*Primary Examiner* — Anne-Marie Falk
(74) *Attorney, Agent, or Firm* — Sughrue Mion, PLLC (57) ABSTRACT

Facing no ethical obstacle and easily to be isolated, multipotent concretely mesenchymal stem cells (MSCs) are one of the most powerful tools in reconstructive medicine. Here the inventors introduced 3D multicelluar spheroids culture construction based on photolithography and micropatterning techniques to improve multipotent differentiation efficiency of MSCs to adult cells. This invention, the 3D spheroid cultured construction for MSCs, leads to great improve of the differentiation efficiency. This invention relates to a cultured cell construct comprising a support; at least one island on the support; a hydrophilic and cytophobic substance applied on the surface of said support so as to encircle the island; and a spheroid which is derived from MSCs, said spheroid being in contact with the island.

14 Claims, 3 Drawing Sheets

CULTURED CELL CONSTRUCTION CONTAINING SPHEROIDS OF MESENCHYMAL STEM CELLS AND UTILIZATION THEREOF

TECHNICAL FIELD

This invention relates to a construction containing cultured cells, concretely, mesenchymal stem cells (MSCs), and also relates to a process to prepare the construction and bio-devices which use the construction. This invention is useful for diagnosis, reconstructive medicine and drug discovery.

BACKGROUND OF THE INVENTION

It has been well known that adult stem cells promise to have tremendous therapeutic potential in regenerative medicine due to their plasticity of differentiation into multiple cell lineages. In bone marrow, there are certain populations of stem cell sources including hematopoietic stem cells, mesenchymal stem cells (MSCs), and multi-potent adult progenitor cells [1. Evans M, Kaufman M. Establishment in culture of pluripotent cells from mouse embryos. Nature 1981; 292: 154-156.; 2. Thomson J A, Itskovitz-Eldor J, Shapiro S S et al. Embryonic stem cell lines derived from human blastocysts. Science. 1998; 282:1145-1147.; 3. E. L. Herzog, C. Li, D. S. Krause, Plasticity of marrow-derived stem cells, Blood 102: 3483-3493.; 4. Petersen B E, Bowen W C, Patrene K D, Mars W M, Sullivan A K, Murase N, Boggs S S, Greenberger J S, Goff J P. 1999. Bone marrow as a potential source of hepatic oval cells. Science 284:1168-1170.].

Under appropriate conditions and stimulations, bone marrow mesenchymal stem cells can differentiate into various cell lineages, such as adipocytes, osteocytes, chondrocytes, myocytes, hepatocytes, astrocytes, or neurons [5. M. Owen, A. J. Friedenstein, Stromal stem cells: marrow-derived osteogenic precursors, Ciba Found. Symp. 136 (1988) 42-60.; 6. Y. Muguruma, M. Reyes, Y. Nakamura, T. Sato, H. Matsuzawa, H. Miyatake, A. Akatsuka, J. Itoh, T. Yahata, K. Ando, S. Kato, T. Hotta, In vivo and in vitro differentiation of myocytes from human bone marrow-derived multipotent progenitor cells, Exp. Hematol. 31:1323-1330.; 7. M. C. Galmiche, V. E. Koteliansky, J. Briere, P. Herve, P. Charbord, Stromal cells from human long-term marrow cultures are mesenchymal cells that differentiate following a vascular smooth muscle differentiation pathway, Blood 82 (1993) 66.76.]. Thus pluripotent MSCs are an attractive source in the field of tissue regeneration and engineering, particularly because the use of embryonic stem cells is limited by ethical considerations.

Another advantage of MSCs is that MSCs can be easily isolated from bone marrow. These characteristics together indicate that MSCs can be used as a powerful tool in reconstructive medicine [8. S. P. Bruder, D. J. Fink, A. I. Caplan, Mesenchymal stem cells in bone development, bone repair, and skeletal regeneration therapy, J. Cell Biochem. 56 (1994) 283-294.; 9. Barry F P, Murphy J M. Mesenchymal stem cells: clinical applications and biological characterization. Int J Biochem Cell Biol. 36:568-584.; 10. Barry F P. Biology and clinical applications of mesenchymal stem cells. Birth Defects Res Part C Embryo Today. 69:250-256.; 11. Song L, Tuan R S, Transdifferentiation potential of human mesenchymal stem cells derived from bone marrow, FASEB JOURNAL 18 (6): AP 2004.; 12. Tocci, A. and Forte, L.: Mesenchymal stem cell: use and perspectives. Hematol. J., 4, 92-96 (2003); 13. M. F. Pittenger, A. M. Mackay, S. C. Beck, R. K. Jaiswal, R. Douglas, J. D. Mosca, M. A. Moorman, D. W. Simonetti, S. Craig, D. R. Marshak, Multilineage potential of adult human mesenchymal stem cells, Science 284 (1999) 143-147.; 14. Y. Jiang, B. N. Jahagirdar, R. L. Reinhardt, R. E. Schwartz, C. D. Keene, X. R. Ortiz-Gonzalez, M. Reyes, T. Lenvik, T. Lund, M. Blackstad, J. Du, S. Aldrich, A. Lisberg, W. C. Low, D. A. Largaespada, C. M. Verfaillie, Pluripotency of mesenchymal stem cells derived from adult marrow, Nature 418 (2002) 41-49.].

Although these characteristics make MSCs very promising in reconstructive medicine, some disadvantages prevent their widespread use. Generally, there are many limitation of using MSCs to clinical applications, including the low differentiation efficiency of MSCs to adult cell lineage. Part of the reason is because of the traditional 2D culture and differentiation methods. At present MSCs research field, the conventional protocols of 2D culture and differentiation method was widely applied.

There still exist some disadvantages in application of 2D monolayer culture system, although many progresses have been achieved. Because the culture area is always limited, the produced amount of differentiated MSCs from this 2D monolayer system is extremely low. Furthermore, the fate of stem cells is regulated by their niche which includes both intrinsic and extrinsic signals [15. Watt F M, Hogan B L. O. Eden: Stem cells and their niches. Science 2000; 287:1427-1430.]. The conventional protocols of 2D culture and differentiation method yields some single cells (singlets) which have been separated from their neighbors, and thus cause the misleading controlling of stem cell differentiation pathways [16. Mueller-Klieser W. Three-dimensional cell cultures: from molecular mechanisms to clinical applications. American Journal of Physiology, 273: 1109-1123.; 17. Kunz-Shughart L A, Kreutz M & Knuechel R. Multicellular spheroids: a three-dimensional in vitro culture system to study tumor biology. International Journal of Experimental Pathology, 79: 1-23.; 18. Kunz-Shughart L A. Multicellular tumor spheroids: intermediates between monolayer culture and in vivo tumor. Cell Biology International, 23: 157-161.; 19. Bates R C, Edwards N S, Yates J D. Spheroids and cell survival. Critical Reviews in Oncology/Hematology, 36: 61-74.; 20. Layer P G, Robitzki A, Rothermel A et al. Of layers and spheres: the reaggregate approach in tissue engineering. Trends in Neurosciences, 25: 131-134.].

The low differentiation efficiency limits further application of MSCs in cell therapy, tissue engineering and other regenerative medicine aspects.

SUMMARY OF THE INVENTION

Facing no ethical obstacle and easily to be isolated, multipotent MSCs are one of the most powerful tools in reconstructive medicine. But the low differentiation efficiency limits further application of MSCs in cell therapy, tissue engineering and other regenerative medicine aspects. Here the inventors introduced 3D multicellular spheroids culture construction based on photolithography and micropatterning techniques to improve multipotent differentiation efficiency of MSCs to adult cells. 3D multicellular spheroids of MSCs in precise uniformed quality cultured on the microdomain substrates were induced into adipocytes and osteoblasts. This invention, the 3D spheroid cultured construction for MSCs, leads to great improve of the differentiation efficiency when compared with the conventional 2D monolayer culture method and other 3D culture system constructed from porous biomaterials.

In connection with micropatterned substrates in which islands are provided on a substrate, a part of the inventors has already filed a patent application (WO 2003/010302) relating to a technique for cultivating various parenchymal cells together with feeder cells (endothelial cells or fibroblasts) on the islands to obtain a spheroid. In this patent document, a stem cell is described as a parenchymal cell to be cultured, which relates to co-cultivation with feeder cells, and other embodiments are not disclosed.

In this invention, this kind of easy control 3D spheroids culture system on micropatterned substrates, which developed by the inventors, were applied to increase the MSCs differentiation efficiency.

Specifically, the present invention provides a cultured cell construct comprising a support;
at least one island on the support;
a hydrophilic and cytophobic substance applied on the surface of said support so as to encircle the island; and
a spheroid which is derived from MSCs, said spheroid being in contact with the island.

In addition, the present invention provides a process for preparing the cultured cell construct comprising the steps of:

(1) putting the MSCs on the island with culture medium, and
(2) cultivating the MSCs and culture medium to form spheroid that is in contact with the island.

Furthermore, the present invention provides a bio-device which comprises the cultured cell construct.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 2A and 2B are color micrographs which show cultivated 3D MSCs spheroids on the microdomains of FIG. 1.

DETAILED DESCRIPTION OF PREFERRED EMBODIMENT

[Cultured Cell Construct of the Present Invention]

The cultured cell construct of the present invention comprise a micropatterned substrate in which islands are provided on a substrate, and spheroids derived from MSCs, said spheroids being in contact with the islands, as described above.

(1) Micropatterned Substrates (a) Surface which Encircles the Islands of the Micropatterned Substrates In order to evade a possibility that cultures of MSCs which are cultivated in islands come into contact with each other, which leads to failure of formation of spheroid, this invention provides a surface, produced by hydrophilic and cytophobic substance, which encircles said island. Details of such a substance are mentioned later. Attention is drawn to the fact, for the present, that, although the above-mentioned U.S. Pat. No. 5,976,826 teaches that sialic acid, lectin, polygalactose and other carbohydrates mediate cell binding, and although P. H. Weigel et al., J. Bio. Chem. Vol. 254 (1979) 10830-10838 exemplifies the fact that hepatocytes are specifically adhered to saccharide which has covalently bound to flat polyacrylamide gel, what is called "cytophobic substance" in this invention is sometimes independent of, or even opposite to, these teachings.

Concretely, hydrophilic and cytophobic substance in accordance with this invention has properties as follows: MSCs cannot adhere to a surface which is made of said hydrophilic and cytophobic substance under cultivation conditions as mentioned later, or, even though adhered, said MSCs can be easily detached by mild cleansing or rinsing. A part of substance which is capable of forming such a surface as mentioned above may be a substance which forms a cytophobic or biophobic monomolecular layer. Preferable examples include compounds which contain a portion of polyethylene glycol (hereinafter may sometimes be referred to as "PEG").

Furthermore, what is preferably used as cytophobic substance in this invention and gives a much more unique feature to this invention is saccharide derivative or peptide derivative each of which is based on a polyethylene glycol segment to one of whose terminals is covalently bound a mono- or oligosaccharide or a certain kind of oligopeptide each of which constitutes a binding domain of ligand to cell surface receptors, or polysaccharide, although it is said that MSCs adhere to saccharides.

Hence, a surface which encircles the above-mentioned islands is preferably made of polymer based on PEG segment. The phrase "based on PEG segment" means that said polymer, when it has no sugar residue, comprises PEG segment so that thus formed surface is covered mainly with free chain of PEG segment. So long as such an action is exerted, said polymer may be homopolymer, block copolymer or a derivative thereof. Incidentally, "free chain" means a state of polymer chain in which said segment can take a substantially free conformation when placed in an aqueous medium.

Although not restrictive, such a polymer, or sugar derivative which has a sugar residue, or peptide derivative which has an oligopeptide residue has the following general formula (I):

$$Y-L^1-(B)_m-L^2-(CH_2CH_2O)_n-L^3-X \qquad (I)$$

In the above-mentioned formula, $L^1$, $L^2$ and $L^3$ independently denote valence bond, oxygen atom or linker with the proviso that, when m is 0 (zero), $L^1$ and $L^2$, taken together, may denote valence bond, oxygen atom or linker.

B denotes a compound of the following formula:

wherein $R^1$ and $R^2$ independently denote a hydrogen atom or an alkyl group having one to five carbon atoms; p denotes an integer of 2 to 5; X denotes a hydrogen atom, a sugar residue or a peptide residue; Y denotes a hydrogen atom or a functional group which is capable of binding or adhering said polymer to the surface of device; m denotes an integer of 0-10,000; and n denotes an integer of 10-20,000.

As for $L^1$, $L^2$ and $L^3$, $L^1$ denotes a valence bond or a linker of $-(CH_2)_q-O-$, $-(CH_2)_q-COO-$, $-(CH_2)_q-S-$ or $-CO-(CH_2)_q-NH-$. When m denotes 0 (zero), $L^1$ and $L^2$, taken together, denote a linker as defined above with respect to $L^1$. Incidentally, the mark q denotes an integer of 2 to 6. When m is other than 0 (zero), $L^2$ denotes $-O-$ or $-O-CH_2CH_2-O$. $L^3$ denotes a valence bond or $-(CH_2)_r-$ wherein r may denote an integer of 1 to 6.

As the above-mentioned polymer, there may be used the polymers as are shown in WO 96/32434 (or U.S. Pat. No. 5,037,969) which was disclosed by a part of inventors of the present invention, WO 96/33233 (or U.S. Pat. No. 5,925,720) and WO 97/06202 (or U.S. Pat. No. 5,929,177) and in Jo et al., Biomaterials, 21, 605-612, 2002, or a slight modification of these polymers, or polymers which are to be produced in a way similar to these patents or document.

In this invention, a polymer of the above-mentioned general formula (I) wherein X denotes a sugar residue, e.g., monosaccharides or oligosaccharides (which may have up to 11 sugar units, preferably up to seven), in particular disaccharides, which constitute a binding domain of ligand to cell surface receptors, is preferably used since a surface which is formed from such a polymer effectively prevents the adhesion of what is called cultivated cells in this invention. A polymer wherein X denotes monosaccharides is disclosed in the above-mentioned WO 96/32434 (or U.S. Pat. No. 5,037,969). In accordance with the method as mentioned in this WO 96/32434, any sugar residue as desired can be made to be supported. A slight modification of said method gives a polymer wherein X denotes polysaccharide residue or oligosaccharide residue. A polymer wherein X denotes sugar residue can also be obtained by another method as disclosed in the above-mentioned WO 96/33233 (or U.S. Pat. No. 5,925,720), according to which acetal group of a polymer having an acetal group at X is converted into aldehyde group, which in turn is subjected to a reductive amination reaction with an amino group which has previously been introduced into mono- or oligosaccharide. As said mono- or oligosaccharides, those which contain at least one galactopyranosyl are preferably used. Although non-restrictive, examples of such oligosaccharides include lactose and various kinds of sialooligosaccharide. Hydrophilic polymer of the above-mentioned general formula (I) wherein X denotes an oligopeptide residue which constitutes a binding domain of ligand to cell surface receptors is also preferably used in this invention. Said ligand may be lectin water-soluble signal molecule (e.g., protein hormone, growth factor protein). As examples of such an oligopeptide, there may be mentioned, although non-restrictive, one which is composed of up to 10 amino acid residues including at least arginine (Arg), glycine (Gly) and aspartic acid (Asp), and which can be water-soluble as a whole.

In addition to the above-mentioned sugar derivatives of polymer based on PEG to which sugar has been covalently bound, polysaccharide per se such as polygalactose, sialic acid and others to which lectin can bind may be used as a hydrophilic polymer in this invention. Anyone skilled in the art would see what hydrophilic polymer is like, from the above-recited polymers. Under cell-cultivation conditions of this invention, hydrophilic polymer means either a polymer the whole of which is water-soluble under an ambient condition, or a polymer wherein polymer (polyethylene in the above-mentioned example) which corresponds to polymer-constituting segment is water-soluble. Those skilled in the art would be able to easily choose concrete polymer which is conveniently usable in this invention, from the above-mentioned polymers in the light of Examples which are mentioned later.

Y, or Y-L.sub.1-(B)— under circumstances, in general formula (I) may be chosen suitably according to the properties of substratum (base plate, film, coating film or deposited film which forms directly or indirectly a surface of culture support or a surface of device) on which a surface of said hydrophilic substance is to be formed. For instance, said surface of culture support may have a surface to which a polymer of general formula (I) can surely be adhered or bound. Although non-restrictive, when said surface of culture support is coated with silicone, or when a surface which has hydroxyl group has been rendered hydrophobic by silane treatment, Y-$L^1$-(B)— may be so selected as to form a block copolymer wherein m denotes an integer other than 0 (zero), e.g., five or more, in the general formula (I), and, thus, with use of the hydrophobicity of thus obtained ester segment, said polymer may be adhered to said surface of culture support to make a surface of hydrophilic substance. In such an instance, when, with a view to enhancing the adhesion of polymer, a homopolymer which corresponds to said ester segment is previously adhered to the surface of support and then said block copolymer is adhered, there is obtained a surface of hydrophilic substance which shows good resistance to peeling etc.

The group Y may be another functional group which reacts with functional group on a surface of support to form a covalent bond such as $-CONH-$, $-CONHCO-$, $-S-S-$, $-O-$, $-Si-O-$, $-NH-$, etc. How to introduce such a functional group to Y, and how to provide a surface of support which has a functional group are partially given in the above-mentioned U.S. Pat. No. 5,976,826. Such a surface of support can also be prepared by subjecting a surface which has been coated with polyamide, polyurethane, polyacrylamide, etc., to plasma treatment by any known method, or by subjecting a monomer which has a protected functional group corresponding to the above-mentioned functional groups to any known plasma treatment and, if necessary, eliminating the protective group.

When, on the other hand, the surface of support is made of metal such as gold, silver and copper, the group Y is desirably a mercapto group, by which a polymer of the general formula (I) can be adhered to substratum through so-called chemical adsorption, and, thus, a desired surface can be produced.

(b) Islands

The above-mentioned islands on the micropatterned substrates are subject to no restrictions so long as the surface of the micropatterned substrates achieves the purpose of this invention. Generally, however, the island may have any shape including circle, polygon such as quadrilateral, ellipse, etc., that has an area of about 2,500 to about 160,000 μm$^2$, preferably about 10,000 to about 90,000 μm$^2$. Circular shape is preferable, in which case the circle has a diameter of about 50 to about 400 μm, preferably about 100 to 300 μm, more desirably about 150 to about 200 μm.

Interval of thus produced islands is preferably about 50 μm at least. When plural islands are separated, at this interval, by surface domain of hydrophilic polymer, there occurs substantially no connection or crosslinkage among cultivated MSCs spheroids, on the above-mentioned islands. The passage "there occurs substantially no connection or crosslinkage" means that the morphological connection of spheroids of cultivated hepatocyte with one another on a large number of islands accounts for less than 10%, preferably less than 5%, more desirably 0%.

If necessary, the above-mentioned islands may be treated so that their surfaces may be cytophilic. The term "cytophilic" in this specification means that, when MSCs are cultivated on a surface having such a property, thus cultivated cells adhere, and thus adhered cells are not detached by mild cleansing or rinsing. Such a surface may be formed of a compound which has hydrophobic group (e.g., hydrocarbon group, alkyl silyl group, alkyl fluoride group, etc.) or a compound (including protein which constitutes extracellular matrix) which has charged group (e.g., —COO$^-$, —PO$_3$H$^-$, etc.). Such a surface can be prepared by replacing hydrophilic substance (or hydrophilic polymer) with one of the above-recited compounds in the above-mentioned process for producing a surface of hydrophilic substance.

Islands having a cytophilic surface can be produced by any method well known to those skilled in the art, such as a pattern-forming method and a micropatterning method. Preferably, however, islands having a cytophilic surface are produced in the following manner: a surface of hydrophilic polymer is formed on a suitable support, and, on this surface, there is placed a pattern on which holes corresponding to islands are arrayed in a desired manner, and, via these holes, a plasma treatment with use of H$_2$+N$_2$ is conducted to remove polymer layer which has formed said surface, and, then, thus obtained islands are, if necessary, treated with a compound which may form the above-mentioned cytophilic surface. The above-mentioned term "if necessary" is intended to mean that, if a surface (which may be a surface of substrates per se) on which a surface of hydrophilic polymer has been placed is a cytophilic surface which yields to no adverse effect from the above-mentioned plasma treatment, the above-mentioned optional treatment is needless.

Exemplarily, the micropatterned substrates can be produced by the steps as follows:

(A) The surface of a support on which MSCs to be cultivated is coated, by spin coating, with a solution, in an organic solvent (such as toluene) or water, of a polymer based on PEG segment, preferably a polymer of the above-mentioned general formula (I), especially desirably a polymer of said formula wherein X denotes a sugar residue or an oligopeptide residue. When the surface of said support is made of glass, if hydroxyl group on said surface is previously rendered hydrophobic by a treatment with a hydrophobic silane coupling agent, subsequent treatment to render islands cytophilic may sometimes become needless. Silane treatment may be conducted by any known method, e.g., the one which is mentioned in H. Otsuka et al., Biomacromolecules, 2000, 21-27. Incidentally, a sugar residue may be introduced into the above-mentioned polymer by the following method: a polymer of the general formula (I) wherein X denotes acetal is previously applied by spin coating; later, amino group of a sugar into which the amino group has previously been introduced is subjected to a reductive amination reaction with aldehyde which has been exposed by the deblocking of the above-mentioned acetal. It is hard to specify the thickness of the resultant polymer layer since optimum thickness varies depending on the species of polymer used. Anyway, a polymer layer is required to have a thickness which prevents adhesion between MSCs, on an island and corresponding cells on another island. Any skilled person would be able to determine such a thickness by a simple experiment. Although non-restrictive, a thickness of a general monomolecular film would be a minimum.

(B) On the surface which has been obtained in step (A), a mask pattern which has plural holes of islands is placed, and a plasma treatment is conducted with use of H$_2$+N$_2$ by a plasma generator, and, thus, polymer layer of domains corresponding to the holes are destructed and removed, and, for instance, hydrophobic-treated surface is exposed.

(C) If necessary, the surface which has been exposed by the removal of polymer layer may be either subjected to plasma polymerization with a monomer having a cytophilic group via the above-mentioned mask pattern, or coated with a polymer derived from said monomer, thus to be modified cytophilic.

In addition to the above-mentioned process for producing the micropatterned substrate by using plasma treatment, the substrate can also be produced by using photolithography technique. In this technique, a polymer having photosensitive groups is applied on a substrate, and then, an optical mask (for example, quarts glass mask) having a desire pattern is placed on the substrate and irradiation of a light to which the above photosensitive polymer react is carried out to cause calcification of the unmasked portion of the surface. Subsequently, the mask is removed and uncalcified part of the photosensitive polymer is removed, so that a desired pattern of islands can be effectively produced. The photosensitive group includes, for example, a methacryloyl group, and an acryloyl group. The principal chain of the polymer is "a hydrophilic and cytophobic substance" as described above, in the present invention. For example, the photosensitive polymer is introduced into one or both of the terminals of a hydrophilic and cytophobic substance to obtain a photosensitive polymer. Islands which presents as a pattern are preferably coated with the cytophilic substance as described above, according to need.

In this way, the micropatterned substrates can be manufactured.

(2) MSCs Spheroid

MSCs (mesenchymal stem cells) are derived from bone marrow, placenta, umbilical cord blood, etc. of mammals such as mouse or human, and can be obtained as conventional methods, for example, can be obtained as adhesive cells derived from myelomonocytic cells, or by carrying out cell separation of myelomonocytic cells by using the cell surface antigen as an index. MSCs strains which have been registered in cell banks or are commercially available may also be used in the present invention.

In the present invention, a desired spheroid can be obtained on the islands by suspending MSCs in a basal medium, filling the islands with the suspension, and culturing them under usual conditions for culturing mammalian cells (for example, at 37° C., 5% CO$_2$). Culture mediums having known compositions may be used as a basal medium, or commercially available culture medium can also be used, as described below.

It can be possible to induce differentiation of MSCs to osteoblasts by carrying out cultivation of MSCs in a culture medium to which dexamethasone, vitamin D and BMP-2 (bone morphogenetic protein-2) have been added, or it can be possible to induce differentiation of MSCs to adipocytes with high probability by carrying out cultivation of MSCs in a culture medium to which 1-methyl-3-isobutylxanthine, dexamethasone, insulin and indomethacin have been added. In addition, it can be possible to induce differentiation of spheroids to chondrocyte by cultivating spheroids under a serum-free condition with adding TGF (transforming growth factor)-β3.

Differentiation induction of MSCs to osteoblasts, adipocytes, or chondrocytes can be freely carried out by changing culture conditions.

A spheroid which is formed from a culture of some species of cells means, as is known from the term "spheroid", a substantially spherical agglomerate of cultivated parenchymal cells, including not only a completely spherical shape but also a slightly flat one.

(3) Bio-Device

Thus obtained culture cell construct of this invention is usable either for bio-devices whose surface is made of a cultivated cell construct per se which has the MSCs spheroids on the surface of a support, or for bio-devices whose surface is formed from said MSCs spheroids. Although not restrictive, examples of such bio-device include a device for the test of toxicity of cultivated MSCs spheroid cells, a device for the screening of substances which activate the function of cultivated MSCs spheroid cells, a device for medical support of the deficiency of cultivated MSCs spheroid cells and a device for trial examination of the physiological activity of cultivated MSCs spheroid cells.

(4) Isolated Spheroids

Spheroids from MSCs which is contained in the aforementioned culture cell construct can be peeled off the support by a physical or biochemical treatment. Thus peeled culture per se is an embodiment of this invention, and is usable in transplantation, organo-regeneration engineering and hybrid-type prosthesis.

[Preparation Process of the Present Invention]

The process for preparing the cultured cell construct according to the present invention comprises the steps of:

(1) putting the mesenchymal stem cells on the island with culture medium, and (2) cultivating the mesenchymal stem cells and culture medium to form spheroid that is in contact with the island.

In the present preparation process, differentiated spheroids can be obtained in condition where the spheroids are in contact with the islands of the substrate as described above, by cultivating MSCs in the islands, i.e., by cultivating MSCs in a basal medium without any feeder cells, and then cultivating MSCs in a culture medium to which differentiation inducing substances as described above have been added, under usual conditions for mammalian cells.

EXAMPLES

This invention is further explained by concrete examples as follows. The examples are provided only with a view to facilitating the understanding of this invention.

A. Production of Cultured Cell Construct

Figure 1:
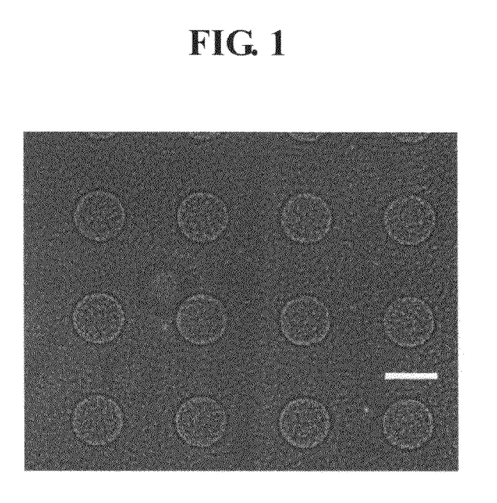
FIG. 1 is a color micrograph which shows the micropatterned substrates with round shape microdomains.

1. Micropatterned Substrates and 3D MSCs Spheroids 0.3% collagen solution was prepared firstly, then was pre-coated onto glass plates in 22 mm diameter and fully spread over the surface. The plates were incubated in cell culture condition for gelation about 2 hours, and were dried at 37° C. for about 2 days. P-PEG (Toyogosei) was then spin-coated onto the collagen coated substrates ($1^{st}$: 500 rpm for 5 s, $2^{nd}$: 3000 rpm for 30 s), dried on hot plate at 60° C. The P-PEG coated substrates were irradiated by UV light, then developed and resined in water. Finally, the developed substrates were dried the on hot plate at 60° C. for the following cell culture. As shown in FIG. 1, the substrates with round shape microdomains were exactly prepared. The scale bar is 100 μm. The diameter of each microdomain was 100 μm and the distance between every two neighboring domains was also 100 μm.

Commercial human MSCs (Cambrex) of passage 5 were inoculated onto the microdomain substrates with the density of $3\times10^5$/substrate and $6\times10^5$/substrate in Mesenchymal Stem Cells Basal Medium (Cambrex). After the spheroids formation, the medium were changed regularly every 3 days.

Figure 2A:
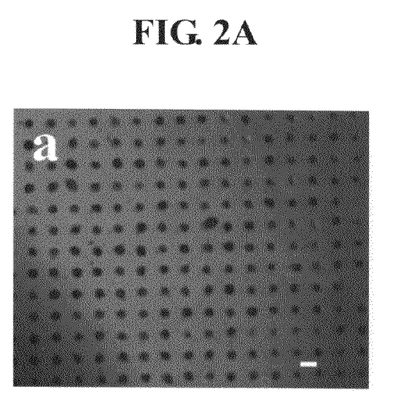
FIG. 2A is a low-magnification image and FIG. 2B is a high-magnification image of the 3D MSCs spheroids.
Figure 2B:
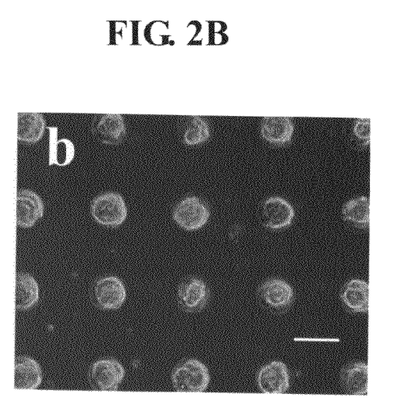

As shown in FIGS. 2A and 2B, human MSCs (also refer as hMSCs) could aggregate together and formed into 3D spheroids on P-PEG substrates of precise size and quality. The scale bar is 100 μm. FIG. 2A is a low magnification image, and FIG. 2B is a high magnification image. The spheroids were not deconstructed even after long period culture (at least 30 days) As for hMSCs, higher cell density ($6\times10^5$/substrate) was more optimal than lower density ($3\times10^5$/substrate, data not shown). Reflecting from Live/Dead staining results (Data not shown), cell in 3D spheroids maintained high viability after 30 plus days culture (Data not shown). Multi-cellular 3D spheroids of MSCs were thus prepared on the specific micro-patterned domains on these substrates, and then were induced into adipocytes and osteoblasts.

B. Differentiation of 3D MSCs Spheroid

[Fundamental Experiments]

(1) Adipogenic Differentiation

Fresh supplemented medium should be made for each usage or medium change. The amount of medium for a 12-well plate is 1 mL/well and the initial inoculation cell density is $3.7\times10^4$/well. Medium was replaced every 3 days with Basal Medium until 100% confluency was reached. When the cells were 100% confluent, 0.5 mL Adipogenic Differentiation Medium (R&D Systems) which containing L-Glutamine and Dexamethasone was then replaced in each well to induce adipogenesis. Fresh Adipogenic Induction Medium should be replaced every 3 days, and then Adipogenic Maintenance Medium. The medium change was repeated 3 rounds. After 5-7 days, lipid vacuoles will start appearing in the induced cells. The appearance of vacuoles can be monitored by microscopic examination. After 7 days, adipocytes can be fixed and saved for Oil Red-O staining.

(2) Osteogenic Differentiation

Fresh supplemented medium should be made for each usage or medium change. The amount of medium for a 12-well plate is 1 mL/well and the initial inoculation cell density is $7.4\times10^3$/well. Medium was replaced every 3 days with Basal Medium until 50-70% confluency was reached. When the cells were 50-70% confluent, 0.5 mL fresh Osteogenic Differentiation Medium (R&D Systems) which containing L-Glutamine and Dexamethasone and Ascorbate was then replaced in each well to induce osteogenesis and then changed every 3 days. After 7 days (or when cells start to detach), osteocytes can be ethanol fixed and stained with Alizarian Red.

[Differentiation of MSCs 3D Spheroid in Staining]

(1) Oil Red O Staining for Adipocytes

The differentiated cells were fixed in 10% formalin for 10 min after PBS washing, then were stained for 15 min with 1 ml of fresh Oil Red-O solution (Sigma). The results were observed under microscope.

(2) Alizarian Red Staining for Osteoblasts

The cells were fixed with a solution of ice-cold 70% ethanol for 1 h after PBS washing, then were stained for 10 min with 1 ml of Alizarin Red (Sigma) after PBS washing. The results were observed under microscope.

(3) Live/Dead Staining of 3D Spheroids of MSCs

500 μL of the combined LIVE/DEAD assay reagents (Sigma) was added into each well after rinse 3 times with PBS. The samples were then incubated for 40 minutes at 37° C. The stained cells were viewed under laser confocal microscope.

(4) Nile Red Staining and Hoechst 33342 Double Staining

To obtain a measure of the intracellular triacyl-glycerol accumulation, the cells were stained with Nile red dye. After fixation in formaldehyde, the cells were washed with PBS, and stained after addition of Nile red working solution on ice for 30 minutes. After Nile red staining, the cells were then treated with Hoechst 33342 (Sigma) work solution and incubated for 10 min. Finally the cells were washed in PBS, and then observed under confocal microscope.

Figure 3:
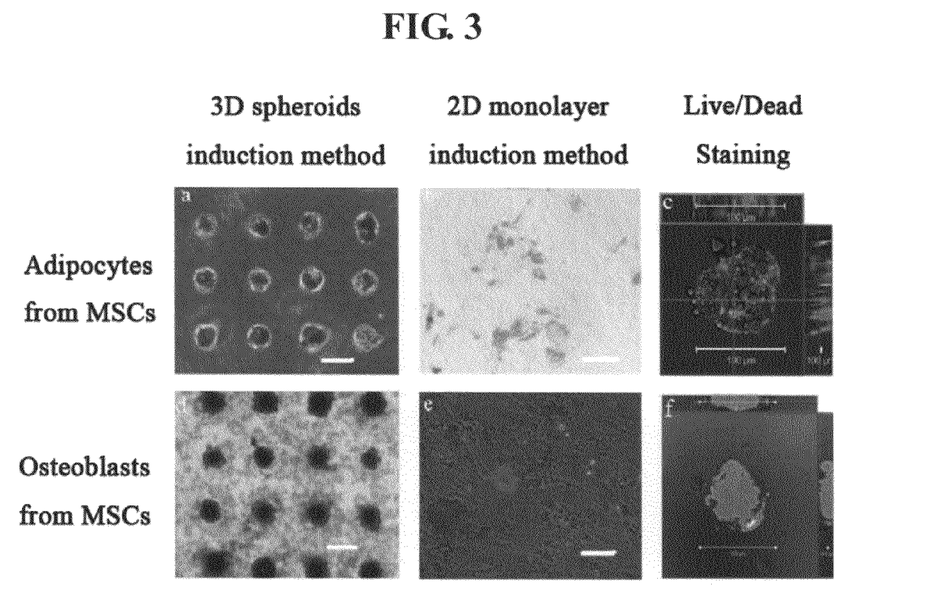
FIG. 3 is a color photograph including color micrographs a-f which show MSCs induced into adipocytes and osteoblasts, comparing 3D spheroid culture with 2D monolayer culture. Micrograph 3a shows oil red staining of MSCs 3D spheroids induced into adipocytes, Micrograph 3b shows oil red staining of MSCs 2D monolayer induced into adipocytes, Micrograph 3c shows live/dead staining of MSCs 3D spheroids induced into adipocytes, Micrograph 3d shows alizarin red staining of MSCs 3D spheroids induced into osteoblasts, Micrograph 3e shows alizarin red staining of MSCs 2D monolayer induced into osteoblasts, and Micrograph 3f shows live/dead staining of MSCs 3D spheroids induced into osteoblasts.

(5) Results of Oil Red O Staining, Alizarian Red Staining and Live/Dead Staining When given suitable stimulations [Janderova L, McNeil M, Murrell A N et al. Human mesenchymal stem cells as an in vitro model for human adipogenesis. Obes Res 2003; 11:65-74./Peter Ebbesen, Vladimir Zachar, Trine Fink, Lisbeth Abildtrup, Kirsten Fogd, Basem M. Abdallah, Moustapha Kassem. Induction of Adipocyte-Like Phenotype in Human Mesenchymal Stem Cells by Hypoxia Stem Cells 2004; 22; 1346-1355], the MSCs of both monolayer culture and 3D spheroid culture group could be induced into adipocytes and osteoblasts. Oil Red O, the specific staining for adipocytes and Alizarin Red, the specific staining for osteoblasts, show that the MSCs were successfully differentiated into adipocytes and osteoblasts (FIG. 3, Micrographs 3a-3f). From the observation of the Oil Red O staining, almost every cell in the spheroids contained Oil Red O positive lipids (Micrograph 3a), whereas only less than 20% cells of the monolayer cultured contained positive lipids (Micrograph 3b). And even after long period of culture and induction, the spheroids of adipocytes from MSCs could still keep high viability in Live/Dead staining (Micrograph 3c). It clearly shows that, when compared with the monolayer induction method, 3D spheroids can improve the differentiation efficiency.

The same conclusion could be drawn from the observation of osteogenic differentiation. The Alizarin Red staining results show that almost every cell in the spheroids were positive for staining (Micrograph 3d), whereas most cells of the monolayer cultured were negative (Micrograph 3e). And even after a long period of culture and induction, the spheroids of osteoblasts from MSCs can still keep high viability in Live/Dead staining (Micrograph 3f).

(6) Results of Double Staining

To determine the definite number of adipogenic differentiated cells in one MSCs spheroid at the same time, and thus to obtain the differentiation efficiency of MSCs, double staining of Nile Red and Hoechst 33342 was carried out. It was applicable to double stain Hoechst 33342 for nuclei and Nile Red for lipids in one MSCs spheroid at the same time. But it was very difficult to count out the exact numbers of differentiated cells because there appear too many lipids in one cell. Although the total number via Hoechst 33342 nuclei staining could be easily obtained, the differentiation rate was difficult to be determined. But with this method it was still possible to get an approximate ratio.

Figure 4:
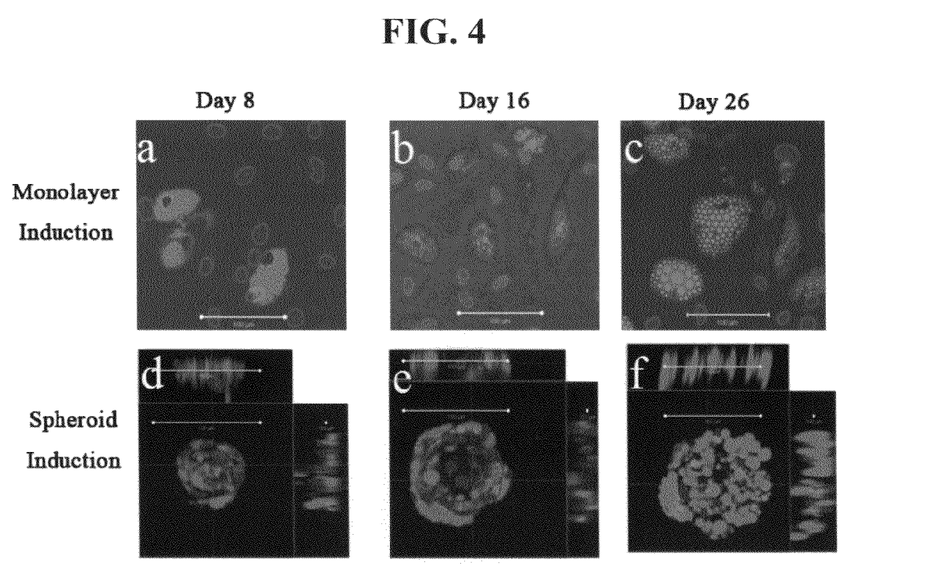
FIG. 4 is a color photograph including color micrographs a-f which show Nile red staining of adipocytes from MSCs, comparing 3D sphenoid culture. Micrograph 4a shows monolayer induced (Day 8), Micrograph 4b shows monolayer induced (Day 16), Micrograph 4c shows monolayer induced (Day 26), Micrograph 4d shows spheroid induced (Day 8), Micrograph 4e shows spheroid induced (Day 16) and Micrograph 4f shows spheroid induced (Day 26).

It could still be concluded that the spheroid induction method improved the differentiation efficiency greatly over 2D monolayer culture methods (FIG. 4, Micrograph 4a-4f). The adipogenic differentiated MSCs at the interior of the spheroids were observed clearly, which show that all MSCs even in the core of spheroids can also be inducted into adipocytes (Micrographs 4d, 4e, and 4f). The time-dependent course of differentiation MSCs to adipocytes were also observed by confocal microscope. At the early differentiation stage (Day 8), big lipids only appeared at the edge of spheroids, but almost all MSCs showed the trend to be inducted (small lipids) (Micrograph 4d). The most pronounced change in the phenotype was observed after 16 days induction. Some obvious lipids appeared in the cells at the core of the spheroids (Micrograph 4e). During the end of differentiation, cells all over the spheroid were filled with lipids, which show the spheroids cultured MSCs were fully differentiated into adipocytes, which was much higher than in monolayer culture controls (Micrograph 4f). At the later differentiation stage (16 day), it was more prevail that the differentiated cell rate among the total cell was much higher in 3D culture group. As reflected in Micrograph. 4b and Micrograph 4e, the total cell numbers, monolayer culture system within the observation scope (about 250 μm×250 μm) and each spheroid (10 um in diameter), was about 15 and 50 by respectively accounting from the double staining confocal images. The differentiated cell in monolayer group was only 7, less than 50% (7/15) of total cells. While in 3D group, almost all of cells were differentiated into adipocytes (100%).

[Differentiation of MSCs 3D Spheroid in Quantitative Measure of RNA Level by RT-PCR]

(1) Experiment Methods

Total RNA was extracted from cultured cells. Standard RT was performed to transcript RNA to cDNA. The cDNA samples were subjected to polymerase chain reaction (PCR) amplification using human specific primers. PPAR-γ2 (also refer as PPAR-γ or PPAR) were chose as special proteins for adipogenic differentiation identification. And ALP were chose as special proteins for osteogenic differentiation identification. The primer sequences were shown as below:

```
PPAR-γ
Forward:
5'-TCAGGTTTGGGCGGATGC-3'          (SEQ ID NO: 1)

Reverse:
5'-TCAGCGGGAAGGACTTTATGTATG-3'    (SEQ ID NO: 2)

ALP
Forward:
5'-GACCCTTGACCCCCACAAT-3'         (SEQ ID NO: 3)

Reverse:
5'-GCTCGTACTGCATGTCCCCT-3'        (SEQ ID NO: 4)
```

Amplification conditions were as follows: Initial denaturation at 94° C. for 5 min followed by 30 cycles of denaturation at 94° C. for 30 sec, annealing at 59-70° C. for 45 sec, extension for 45 sec at 72° C. and a final polymerization at 72° C. for 10 min. Human MSCs of both spheroid and monolayer culture without induction were used as negative controls.

To compare the pattern of differentiating hMSCs to that of human adipocytes and osteoblasts, RT-PCR technique was applied to detect the specific mRNA genes during differentiation of hMSCs. The examination of the relative mRNA levels revealed a pattern of gene expression in hMSCs similar to that of morphology observation results described. PPAR-γ and ALP were chose as special mRNA for the identification of adipogenic and osteogenic differentiation. Human MSCs of both spheroid and monolayer culture without induction were used as controls.

All RT-PCR experiments were performed in triplicate (performed in duplicate). Analysis of statistical significance was performed using a one tailed Student's t-test. Significance was determined using a 95% probability value.

(2) RT-PCR for Adipocytes

In Real-time quantitative PCR for PPAR-γ mRNA expression in differentiated hMSCs cells, the change in expression of PPAR-γ relative to the internal control gene (GAPDH) at various time points was studied. The mean change in expression of the target gene at each time point was calculated using the following equation: The ΔCt values were defined as the absolute value of the difference between the Ct of PPAR-γ and Ct of GAPDH for each sample. The ΔΔCt value was determined by subtracting the ΔCt of vehicle control at each time point from the ΔCt of each sample. The relative fold increase (RFI) of ALP was calculated by the equation: RFI=2−ΔΔCt.

Figure 5:
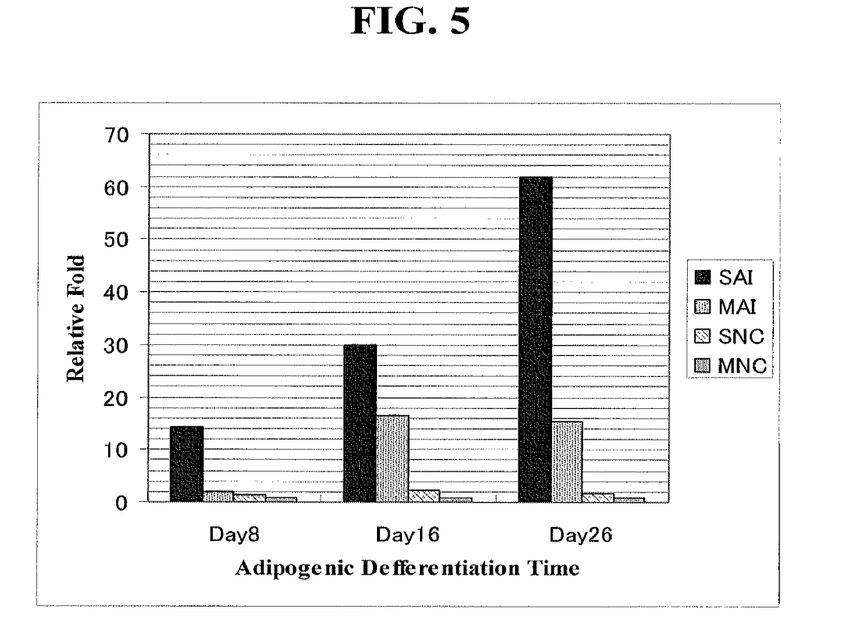
FIG. 5 is a graph which shows real-time quantitative PCR for PPAR-γ mRNA expression in differentiated MSCs. The horizontal axis shows adipogenic differentiation time and the vertical line shows relative fold of mRNA expression.

The adipocyte-specific RNA expression level of PPAR in 3D cultured differentiation method (SAI group), which was reflected from the value of 2−ΔΔCT (PPAR-GAPDH) (FIG. 5), was about 14.2 times higher at day 8, 30.0 times higher at day 16 and 62.1 times higher at day 26 than those of PPAR expression of monolayer cultured MSCs without differentiation (MNC group). Conversely, in monolayer cultured differentiation group (MAI group), the PPAR expression level was only 2.2 times higher at day 8, 16.6 times higher at day 16 and 15.6 times higher at day 26 than that of control group (SNC group). These relative RNA expression data clearly revealed that, during the adipogenesis, the spheroid cultured methods could greatly improve the differentiation efficiency from MSCs to adipocytes when compared with the monolayer cultured groups.

(3) RT-PCR for Osteoblasts

In Real-time quantitative PCR for ALP mRNA expression in differentiated hMSCs cells, the change in expression of ALP relative to the internal control gene (GAPDH) at various time points was studied. The mean change in expression of the target gene at each time point was calculated using the following equation: The ΔCt values were defined as the absolute value of the difference between the Ct of ALP and Ct of GAPDH for each sample. The ΔΔCt value was determined by subtracting the ΔCt of vehicle control at each time point from the ΔCt of each sample. The relative fold increase (RFI) of ALP was calculated by the equation: RFI=2−ΔΔCt.

Figure 6:
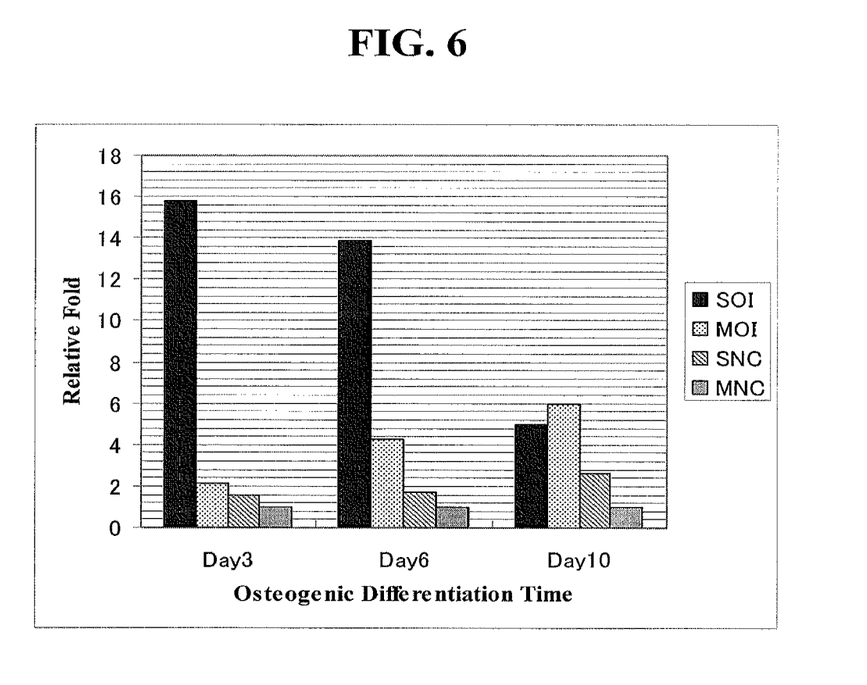
FIG. 6 is a graph which shows real-time quantitative PCR for ALP mRNA expression in differentiated MSCs. The horizontal axis shows osteogenic differentiation time and the vertical line shows relative fold of mRNA expression.

ALP expression of osteogenesis was also tested by the RT-PCR method (SAI group). This osteoblast specific RNA detection results was similar to the results obtained from the adipogenic differentiation (FIG. 6). ALP level of 3D cultured differentiation method was much higher than monolayer induction group during the initial induction period: The RNA expression in 3D spheroids cultured group was about 15.9 times higher at day 3, 13.9 times higher at day 6 and 5.1 times higher at day 11 than those of monolayer cultured MSCs without differentiation (MNC group). While in monolayer cultured differentiation group (MAI group), the ALP expression level was only 2.2 times higher at day 3, 4.2 times higher at day 6 and 5.9 times higher at day 10 than the monolayer control group (SNC group). These relative RNA expression data exactly revealed that, during the adipogenesis, the spheroid cultured methods could greatly improve the differentiation efficiency from MSCs to adipocytes when compared with the monolayer cultured groups.

What is claimed is:

1. A cultured cell construct comprising
a support;
at least one island on the support;
a hydrophilic and cytophobic substance applied on the surface of said support so as to encircle the island; and
a spheroid produced by adhering mesenchymal stem cells to the island, wherein said spheroid is in contact with the island,
and wherein the island has an area of about 10,000 to 160,000 μm².

2. The cultured cell construct according to claim 1, wherein said cultured cell construct contains at least two substantially circular adjacent islands, and wherein the interval between said adjacent islands is at least about 100 to 150 μm.

3. The cultured cell construct according to claim 1, wherein the hydrophilic and cytophobic substance is a polymer based on polyethyleneglycol segment which has a hydroxyl group at one of its terminals.

4. The cultured cell construct according to claim 1, wherein the hydrophilic and cytophobic substance has a polyethyleneglycol segment and a polylactide segment.

5. The cultured cell construct according to claim 1, wherein the hydrophilic and cytophobic substance is selected from the group consisting of polysaccharides and derivatives which are based on a polyethylene glycol segment, to one of whose terminals are covalently bound a compound which is selected from the group consisting of mono- or oligosaccharides and oligopeptides, each of which constitutes a binding domain of ligand to cell surface receptors.

6. The cultured cell construct according to claim 1, wherein the hydrophilic and cytophobic substance is a sugar derivative based on a polyethylene glycol segment, to one of whose terminals are covalently bound mono- or oligosaccharides, each of which contains at least one galactosyl group.

7. The cultured cell construct according to claim 1, wherein the hydrophilic and cytophobic substance is a sugar derivative which comprises a polyethylene glycol segment, to one of whose terminals are covalently bound mono- or oligosaccharides, each of which contains at least one galactopyranosyl group, and a polylactide segment.

8. The cultured cell construct according to claim 1, wherein the hydrophilic and cytophobic substance is a peptide derivative based on a polyethylene glycol segment, to one of whose terminals are covalently bound oligopeptides which comprise an amino acid sequence of arginine-glycine-aspartic acid.

9. The cultured cell construct according to claim 1, wherein the island has a surface which is made of a cytophilic substance.

10. The cultured cell construct according to claim 1, wherein the island has a surface which is made of a cytophilic substance selected from the group consisting of a compound that has a hydrocarbon group, an alkyl silyl group and an alkyl fluoride group; a compound that has a carboxylate anion and a phosphate anion; and a protein that constitutes extracellular matrices.

11. A bio-device comprising a surface formed from a cultured cell construct, said construct comprising a support; at least one island on the support; a hydrophilic and cytophobic substance applied on the surface of said support so as to encircle the island; and a spheroid produced by adhering mesenchymal stem cells to the island, wherein said spheroid is in contact with the island, and wherein the island has an area of about 10,000 to 160,000 μm².

12. The bio-device according to claim 11, wherein said cell culture construct contains at least two substantially circular adjacent islands, and wherein the interval between said adjacent islands is at least about 100 to 150 μm.

13. The bio-device according to claim 11, which is selected from the group consisting of a device for the test of toxicity of spheroid-forming cells, a device for the screening of substance which activates the function of spheroid-forming cells, a device for medical support of the deficiency of spheroid-forming cells, and a device for trial examination of the physiological activity of parenchymal cells.

14. A process for preparing a cultured cell construct, the construct comprising a support; at least one island on the support; a hydrophilic and cytophobic substance applied on the surface of said support so as to encircle the island; and a spheroid which is derived from mesenchymal stem cells, said spheroid being in contact with the island, the process comprising the steps of:
(a) providing a support comprising at least one island on the support, wherein a hydrophilic and cytophobic substance is applied on the surface of said support so as to encircle the island,
(b) putting the mesenchymal stem cells on the island with culture medium, and
(c) cultivating the mesenchymal stem cells and culture medium to form a spheroid that is in contact with the island.

* * * * *

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial
<220> FEATURE:
<223> OTHER INFORMATION: Primer

<400> SEQUENCE: 1
tcaggtttgg gcggatgc                                                 18

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
tcagcgggaa ggactttatg tatg                                          24

<210> SEQ ID NO 3
<211> LENGTH: 19
<212> TYPE: DNA
<213> ORGANISM: Artificial
<220> FEATURE:
<223> OTHER INFORMATION: Primer

<400> SEQUENCE: 3
gacccttgac ccccacaat                                                19

<210> SEQ ID NO 4
<211> LENGTH: 20
```

```
<212> TYPE: DNA
<213> ORGANISM: Artificial
<220> FEATURE:
<223> OTHER INFORMATION: Primer

<400> SEQUENCE: 4
gctcgtactg catgtccct                                              20
```